United States Patent [19]

Gurfinkel et al.

[11] Patent Number: 5,571,916
[45] Date of Patent: *Nov. 5, 1996

[54] PROCESS TO PREPARE DIAZINON

[75] Inventors: Elkana Gurfinkel, Omer; Yaakov Shmueli, Beer Sheva, both of Israel

[73] Assignee: Makhteshim Chemical Works Ltd., Beer-Sheva, Israel

[ * ] Notice: The term of this patent shall not extend beyond the expiration date of Pat. No. 5,231,180.

[21] Appl. No.: 271,988

[22] Filed: Jul. 8, 1994

[30] Foreign Application Priority Data

Jun. 23, 1994 [IL] Israel ......................................... 110096

[51] Int. Cl.$^6$ ..................................................... C07F 9/6512
[52] U.S. Cl. .......................................... 544/243; 544/319
[58] Field of Search .............................................. 544/243

[56] References Cited

U.S. PATENT DOCUMENTS

| | | | |
|---|---|---|---|
| 2,754,243 | 7/1956 | Gysin et al. | 544/243 |
| 3,951,975 | 4/1976 | Hofer et al. | 544/243 |
| 4,066,642 | 1/1978 | Sury et al. | 544/243 |
| 4,326,059 | 4/1982 | Gargano et al. | 544/243 |
| 5,034,529 | 7/1991 | Freeman | 544/243 |
| 5,231,180 | 7/1993 | Gurfinkel et al. | 544/243 |

*Primary Examiner*—Emily Bernhardt
*Attorney, Agent, or Firm*—Browdy and Neimark

[57] ABSTRACT

Diazinon is prepared by coverting the starting hydroxypyrimidine to its potassium salt by reacting it with potassium carbonate in an organic solvent after removal of the water by azeotropic distillation, and reacting the resulting non-aqueous salt with diethyl thiophosphoryl chloride and recovering the diazinon formed, wherein the quantity of potassium carbonate used relative to the starting hydroxypyrimidine is less than molar and desirably of a ratio in the range of 0.55 to 0.75.

22 Claims, No Drawings

PROCESS TO PREPARE DIAZINON

FIELD OF THE INVENTION

The present invention concerns the improved process for preparing diazinon which, owing to its good insecticidal and acaricidal properties, is of great commercial value for the destruction of insect pests.

BACKGROUND OF THE INVENTION

Diazinon was produced for the first time by Glysin and Margot by reacting 2-isopropyl-4-methyl-6-hydroxy-pyrimidine (hereinafter hydroxypyrimidine) with diethyl-thiophosphoryl chloride (hereinafter TPC) in an inert solvent, in the presence of potassium carbonate as described in United Kingdom patent number 713.278.

In this heterogeneous reaction the potassium pyrimidinolate is initially formed by heating the hydroxypyrimidine with potassium carbonate in benzene, with simultaneous removal of the water formed. The potassium salt so produced is then reacted with TPC by heating for several hours, the potassium chloride formed extracted by washing with water, and the solvent removed under reduced pressure.

The standard process for the industrial manufacture of diazinon is carried out essentially by means of a 4-stage synthesis, as described in great detail in U.S. Pat. No. 5,231,180; whose contents are incorporated by its reference herein.

The novel process described in U.S. Pat. No. 5,231,180 involves the reaction of the hydroxypyrimidine with TPC by first mixing the hydroxprimidine with a select group of organic solvents, removing water by azeotropic distillation, adding dry potassium carbonate in a mole ratio of carbonate to hydroxypyrimidine of 1:1 to 1.2:1, and adding less than a stoichiometric amount of TPC to for the diazinon.

While this process afforded fairly pure diazinon, the use of excess potassium carbonate is expensive and a cause for concern in its removal from the waste water.

SUMMARY OF THE INVENTION

It is an object of the invention to overcome deficiencies in the prior art, such as indicated above. It is another object of the present invention to provide an improved method for preparing diazinon. It is a further object of the present invention to provide a method more economical than known methods for the production of diazinon substantially free of toxic by-products in high yields and very high purity, being only very slightly colored.

It has unexpectedly been discovered that diazinon can be prepared by an improved method which comprises reacting wet or dry hydroxypyrimidine with thiophosphorylchloride (TPC) wherein an organic solvent, either methyl-isobutyl ketone (MIBK), aliphatic hydrocarbons or a mixture of both, most desirably petroleum ether having a boiling point of about 60°–140° C., cyclohexane, octane and heptane, is mixed with the hydroxypyrimidine and the water is azeotropically distilled off: dry solid potassium carbonate is added, and when the first mentioned solvent is a hydrocarbon, methyl-ethylketone (MEK) is optionally added; less than a stoichiometric amount of TPC is then added to react with the hydroxypyrimidine to form the desired, diazinon; and the resultant diazinon is the recovered, wherein the improvement consists of using less than one mole of potassium carbonate per mole of hydroxypyrimidine and optionally azeotropically distilling off water during the reaction with TPC.

By means of the present further improved process, there is an appreciable drop in the amount of potassium carbonate needed for the reaction, while retaining a high yield and high purity of the final product.

DETAILED DESCRIPTION OF THE INVENTION

The process of the present invention requires that the reaction of the hydroxypyrimidine with TPC be run in a solvent from which water can be removed azeotropically. Suitable solvents are aliphatic hydrocarbon solvents such as petroleum ether 60–40, petroleum ether 60–80 heptane, octane, hexane or cyclohexane, together with MEK, or instead MIBK can be used as the sole solvent. The ratio of MEK to other solvents may be 1:99 to 1:4. Most preferred as the solvent, however, is either MIBK alone or heptane or octane or a mixture thereof together with MEK.

The improved results of the present reaction are in large measure dependent on the use of potassium carbonate as base, added as a solid. The $K_2CO_3$ is preferably added in a mole ratio of carbonate to hydroxypyrimidine of 0.55 to 0.75, preferably 0.60 to 0.70.

The reaction of the present invention may be run at a temperature of from 60° C. to 116° C. during the preparation of the potassium salt of the hydroxypyrimidine and at a temperature of from 50° C. to 120° C., preferably 80° C. to 100° C. during the subsequent reaction with TPC; and the time of reaction after adding TPC may be from 2 hours to 10 hours, preferably four hours. Contrary to U.S. Pat. No. 5,034,529, excellent yields of high purity product area achieved even when the reaction is carried out on an industrial scale, e.g. in reactors having volumes of 100 liters or more and even in reactors having volumes of more than 1000 liters.

The very high yield of the present invention may be further improved by recycling the unreacted hydroxypyrimidine, making this process even more commercially viable.

While the prior art discloses removing the water either prior to or simultaneously with reacting with TPC, several problems were found to result from such practice. Azeotropic distillation of the water prior to adding TPC using NaOH or KOH was found to require a long period of heating to remove the last traces of water from the solid chunks formed. The solid chunks made it almost impossible to properly stir the mixture after the addition of the TPC. U.S. Pat. No. 4,326,059 attempted to overcome this problem by azeotropically distilling off the water in the presence of a phase transfer catalyst. However, long reaction times were still required and the final product still contained Thiotepp.

U.S. Pat. No. 4,066,642 attempted to overcome this problem by azeotropically distilling off the water simultaneously with the reaction with TPC. The results were long reaction times affording low yields of dark colored diazinon. Even the use of the solvents of the instant invention, but using sodium hydroxide or sodium carbonate, also caused sticking the prevented the formation of a workable suspension.

However, the process of the instant invention involving azeotropic distillation of hydroxypyrimidine in the presence of MIBK or an aliphatic hydrocarbon solvent, followed by adding dry solid potassium carbonate—and, when the first mentioned solvent is an aliphatic hydrocarbon, also MEK provides a product which uses only short reaction times and affords very high yields or almost colorless diazinon, having a very high purity, and without the need for the use of a catalyst.

When a mixed solvent such as aliphatic hydrocarbon/ketonic solvent is used there is no need to continue to remove any water formed during the reaction with TPC. However, when only an aliphatic hydrocarbon solvent is used, the removal of water by azeotropic distillation during the reaction with TPC was found to makedly help to form a purer product.

While there is dome superficial similarity between the method of U.S. Pat. No. 5,034,529 and the process is more advantageous in the production plant when compared to the process of U.S. Pat. No. 5,034,529 because it utilized a much shorter overall reaction time, e.g. the azeotropic distillation is completed in less than 2–3 hours and usually in less than 2 hours. A further advantage occurs due to the use of hydrocarbon/MEK as solvents, as the use of these solvents serves to reduce or avoid the formation of added related impurities which often form by there action at high temperatures between MIBK and a strong base such as sodium hydroxide and potassium hydroxide.

By means of the present process commercially satisfactory reaction rates are achieved with yields of some 98 percent and purity of 97 to 99 percent of diazinon only very slightly colored. This process is, thus, an improvement over the prior art and especially U.S. Pat. No. 5,231,180 in that an appreciably less amount of potassium carbonate affords diazinon in high yield, and purity and low color at lower cost.

While the invention will now be described in connection with certain preferred embodiments in the following examples, it will be understood that it is not intended to limit the invention to these particular embodiments. On the contrary, it is intended to cover all alternatives, modifications and equivalents as may be included within the scope of the invention.

EXAMPLE 1

Laboratory Scale

A mixture of 170 g (1.05M) of 94% wet hydroxypyrimidine and 300 ml heptane were heated to reflux and the water azeoptropically distilled off, over a period of one hour. The mixture was cooled to 70° C., 90 g dry potassium carbonate, and 10 ml MEK, and were added and heated to 95° C. for an hour. To this were added 190 g TPC over 30 minutes and the mixture kept at a temperature of 95° C. for three hours. The mixture was cooled to 70° C., water added, the pH adjusted to 12.5 to 13 with a sodium hydroxide solution, the water layer discharged and the operation repeated. Water was then added again, the pH adjusted to 1.5 to 2 by the use of sulfuric acid solution. After stirring the water was separated and the heptane solvent distilled off to afford 300 g diazinon at a purity of 98.7% in a yield of 97.4%. The diazinon was light straw in color.

EXAMPLE 2

Production Plant Scale

A mixture of 1,300 kg (8.04 kilomoles) hydroxypyrimidine and 3000 liters heptane were heated to reflux in an 8,000 liter stainless steel reactor and the water azeotropically distilled off over a period of three hours. The mixture was cooled to 70° C. and 700 kg of potassium carbonate, and 100 liters MEK, were added. The mixture was heated to 95° C. for an hour, 1,425 kg TPC were added over 30 minutes and the mixture was heated for three hours. The reactor was cooled to 70° C. and of the heptane afforded 2,250 kg of diazinon in a concentration of 98.7% and a yield of 97.4, having a light straw color.

EXAMPLE 3

Process of the Present Invention in the Laboratory

A mixture of 170 g (1.05 moles) hydroxypyrimidine and 280 g MIBK were heated to 115° C. and the water azeotropically distilled off over a period of about two hours. The mixture was cooled to 80° C. and 90 g dry potassium carbonate was added. The mixture was heated to 80° C. for one hour, cooled to 65° C. and 190 g (1 mole) of TPC was added over one hour. The mixture was heated to 80° C. and kept at this temperature for an additional two hours. The mixture was worked up as before, to afford 300 g of a light colored diazinon at a purity of 98.5% and a high yield of about 98%.

EXAMPLE 4

Process of the Present Invention in the Production Plant

A mixture of 1,300 kg (8.04 kilomoles) hydroxypyrimidine and 2,250 kg MIBK were heated at 115° C. and the water azeotropically distilled off over a period of only two hours. The mixture was cooled to 65° C., 700 kg of dry potassium carbonate were added and the mixture heated at 80° C. for one hour. The mixture was cooled to 65° C., 1470 kg of TPC were added over a period of 30 minutes, the mixture was heated to 80° C. and kept at this temperature for three hours. The mixture was worked up as before, to afford 2,312 kg of diazinon in a purity of 98.2% in a yield of 96.2%.

EXAMPLE 5

Process of the Invention in the Production Plant

A mixture of 1,300 kg (8.04 kilomoles) of 94% wet hydroxypyrimidine, 700 kg dry potassium carbonate and 2,250 kg heptane were heated to reflux and the water azeotropically distilled off, over a period of two hours. To this were added 1,470 kg TPC over 30 minutes at reflux and the water azeotropically distilled of over a period of 4 hours. The mixture was cooled to 70° C. water added, the pH adjusted to 12.5 to 13 with sodium hydroxide solution, the water layer discharged and the operation repeated. Water was then added again. The pH adjusted to 1.5 to 2 by the use of sulfuric acid solution. After stirring the water was separated and a heptane solvent distilled off to afford 2,312 kg diazinon at a purity of 98.7% in a yield of 97.4%. The diazinon was light straw in color.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

We claim:

1. A process for preparing diazinon comprising reacting wet or dry 2-isopropyl-4-methyl-6-hydroxypyrimidine with thiophosphoryl chloride (TPC), by mixing said 2-isopropyl-4-methyl-6-hydroxypyrimidine with an aliphatic hydrocarbon solvent selected from the group consisting of petroleum ether having a boiling point of about 60°–140° C., hexane, heptane, octane, cyclohexane and a mixture thereof, and removing water by azeotropic distillation;

then adding dry potassium carbonate to the reaction mixture to convert said 2-isopropyl-4-methyl-6-hydroxypyrimidine to its potassium salt in the absence of water; and adding less than a stoichometric amount of said TPC to form said diazinon, wherein the improvement comprises using a mole ratio of potassium carbonate to 2-isopropyl-4-methyl-6-hydroxypyrimidine of 0.55 to 0.75, and further comprising adding dry methyl ethyl ketone (MEK) following said azeotropic distillation and prior to adding said TPC.

2. A process according to claim 1, wherein, prior to said azeotropic distillation, at least one of said organic solvent and said hydroxypyrimidine is wet.

3. A process in accordance with claim 1, wherein water is azeotropically distilled off during the reaction with TPC.

4. A process in accordance with claim 1, wherein said MEK is added at a concentration of 1%–20% based on total solvent content.

5. A process in accordance with claim 4, wherein said MEK is added at a percentage of approximately 5%.

6. A process is accordance with claim 1, wherein the mole ratio of potassium carbonate to 2-isopropyl-4-methyl-6-hydroxypyrimidine is 0.60 to 0.70.

7. A process in accordance with claim 1, wherein the temperature of reaction is 50° C. to 120° C.

8. A process in accordance with claim 1, wherein the temperature of reaction is 80° C. to 100° C.

9. A process in accordance with claim 1, wherein the time of reaction is 2 to 10 hours.

10. A process in accordance with claim 1, wherein the time of reaction is approximately 4 hours.

11. A process in accordance with claim 1, wherein said azeotropic distillation is completed in less than about 3 hours.

12. A process for preparing diazinon comprising reacting wet or dry 2-isopropyl-4-methyl-6-hydroxypyrimidine with thiophosphoryl chloride (TPC), by mixing said 2-isopropyl-4-methyl-6-hydroxypyrimidine with an organic solvent selected from the group consisting of petroleum ether having a boiling point of about 60°–140° C., hexane, heptane, octane, cyclohexane or a mixture thereof, and removing water by azeotropic distillation;

then adding dry potassium carbonate to the reaction mixture to convert said 2-isopropyl-4-methyl-6-hydroxypyrimidine to its potassium salt in the absence of water; and adding less than a stoichometric amount of said TPC to form said diazinon, wherein the improvement comprises adding dry methyl ethyl ketone (MEK) following said azeotropic distillation and prior to adding said TPC; and adding less than 1 mole of potassium carbonate per mole of 2-isopropyl-4-methyl-6-hydroxypyrimidine and optionally azeotropically distilling off water during the reaction with TPC.

13. A process in accordance with claim 12, wherein said MEK is added at a concentration of 1%–20% based on total solvent content.

14. A process in accordance with claim 13, wherein said MEK is added at a percentage of approximately 5%.

15. A process according to claim 12, wherein the reactor has a volume of at least 100 liters.

16. A process according to claim 12, wherein the reactor has a volume of at least 1000 liters.

17. A process according to claim 12, wherein the temperature of reaction is 50° C. to 120° C.

18. A process according to claim 12, wherein the temperature of reaction is 70° C. to 90° C.

19. A process according to claim 12, wherein the time of reaction is 2 to 10 hours.

20. A process according to claim 12, wherein the time of reaction is approximately 6 hours.

21. A process according to claim 12, wherein said azeotropic distillation is completed within 2 to 3 hours.

22. A process in accordance with claim 12, wherein water is azeotropically distilled off during the reaction with TPC.

* * * * *